United States Patent [19]

Shah et al.

[11] 4,093,867
[45] June 6, 1978

[54] APPARATUS FOR AUTOMATICALLY CALIBRATING AND TESTING SMOKE DETECTORS

[75] Inventors: Mahesh J. Shah, Bridgeport; Joseph P. Mallozzi, Norwalk, both of Conn.

[73] Assignee: General Signal Corporation, Rochester, N.Y.

[21] Appl. No.: 736,036

[22] Filed: Oct. 27, 1976

[51] Int. Cl.² .............................................. G01N 21/26
[52] U.S. Cl. ..................................... 250/576; 356/207
[58] Field of Search ........................ 356/201, 204–208; 250/252, 573, 574, 575, 576; 340/237 S

[56] References Cited

U.S. PATENT DOCUMENTS 3,702,734  11/1972  Lindahl et al. ...................... 356/207
4,009,376  2/1977  Faraguet .............................. 250/252

Primary Examiner—David C. Nelms
Attorney, Agent, or Firm—Milton E. Kleinman; John Ohlandt

[57] ABSTRACT

Apparatus for automatically calibrating smoke detectors within desired ranges of values of smoke obscuration, and thereafter retesting them for valid calibration; in accomplishing this the smoke obscuration is continuously increased at a predetermined uniform rate.

13 Claims, 4 Drawing Figures

APPARATUS FOR AUTOMATICALLY CALIBRATING AND TESTING SMOKE DETECTORS

BACKGROUND, OBJECTS AND SUMMARY OF THE INVENTION

The present invention pertains to a system comprising apparatus especially adapted to perform automatically a required calibration step so as to calibrate smoke detectors. More particularly, the present invention is directed to a system that accomplishes automatically both the required calibration and the retesting of such detectors such that they are assured of being completely reliable when placed in actual operation by a customer.

In order to furnish some background for the system or apparatus and to indicate the fundamental intent and purpose of such apparatus, reference may be made to a related patent application Ser. No. 647,018, which application involves a smoke detector featuring a balanced bridge network used to initiate an alarm when a difference is sensed between a pair of photocells which are effected by smoke obscuration in a chamber provided in such smoke detector. The bridge network is so arranged that two of the legs thereof are made up of the resistances of the aforesaid pair of photocells, these resistances normally being connected in series between a DC supply and ground. The other two legs of the bridge network are made up of selected portions of the total resistance of a potentiometer, which is likewise connected between the power supply and ground, the potentiometer being supplied with a movable contact for suitably proportioning the potentiometer resistance. It will be clear that the movable contact of the potentiometer is extended through the casing of the aforesaid smoke detector so that an external means such as a screwdriver may be used when an adjustment of the potentiometer resistance is required, as when calibrating the detector. For a detailed understanding of the operation of such a smoke detector, reference may be made of the cited application.

The present invention is particularly adapted to accomplish automatically the required adjustment which will provide calibration in the manufacturing stage of a smoke detector of the aforesaid type. However, it will be apparent to those skilled in the art that the present invention is not strictly limited to the precise type of smoke detector referred to above and can be used in connection with a variety of smoke detectors that have similar adjustment or calibration arrangements.

In any event, regardless of the particular type of smoke detector whose calibration and testing is under consideration, the fact is that uniform standards have been completely lacking in the calibrating and testing of smoke detectors of current design. Thus each manufacture tends to follow his own bent in calibrating and testing such detectors and this has led to severe difficulties when such units are placed into operation by customers. For example, the rate of flow of the smoke that is furnished in the testing operation has often not been carefully controlled with the result that time lags and the like render questionable the precise obscuration levels at which the smoke detectors went into an alarm state.

Accordingly, it is a primary object of the present invention to provide automatic apparatus for the aforesaid purposes such that a high degree of reliability will be assured in the calibration and testing operations.

Another object is to establish control on the degree of smoke obscuration present in a testing chamber. More specifically, it is an object of the invention to increase visible smoke obscuration automatically at an approximate uniform rate of 0.4% per foot per minute.

It is well understood that smoke detectors of current design are often so calibrated that they are meant to respond to smoke obscuration at levels typically between 1.34% and 1.55%. However, as previously noted, the methods and techniques used for calibrating smoke detectors have left much to be desired and it is to the end of proper and precise calibration that the smoke obscuration is automatically increased at a predetermined rate, preferably the aforesaid 0.4% per foot per minute rate. As a result, it is insured that the smoke detectors calibrated and tested in accordance with the present invention will provide the required alarm when they reach the aforementioned range of smoke obscuration.

In essence then, the above objects of the invention are implemented by a primary feature residing in the provision of apparatus comprising an enclosure defining a smoke chamber, such smoke chamber including a reserve smoke compartment for generating a large quantity of reserve smoke, a smoke mixing compartment in which the dense smoke from the reserve compartment is permitted to diffuse and to be drawn in a path which brings a uniform smoke of required density into a test compartment in which a plurality of groups of smoke detectors to be calibrated and tested are disposed.

In the initial determination of the degree of light obscuration that has been achieved by the smoke that has been drawn in, a light source and a photocell are used. Thus the photocell is connected in a suitable circuit that operates to provide a current output equivalent to the smoke level at any time. In addition, from the standpoint of the broad aspect of the present invention, means are also provided for automatically changing the degree of light obscuration produced by the influx of smoke by changing the flow of smoke into the aforenoted test compartment. This means for automatically changing the degree of obscuration includes means for so increasing the obscuration at a precise and predetermined uniform rate. Preferably this rate has been selected to be 0.4% per foot per minute.

Over and above the immediately above-noted components or features, the present invention, in addition to efficiently accomplishing the objective of providing a precise and uniform rate of increase in the obscuration level, achieves the further objective of automatic calibration by including means for increasing the light obscuration to the predetermined calibration range, that is, the range in which a smoke detector device under test should respond and provide the appropriate alarm indication. Further provided are means for calibrating groups of smoke detectors under test by the provision of means for adjusting each of the smoke detectors as the smoke obscuration level reaches the calibration range such that the smoke detectors under test will normally provide their alarm indication. To this end a further feature resides in means which are provided for indicating to the operator whether each detector has in fact been properly calibrated, that is, has given its alarm indication at the appropriate point.

A further specific feature resides in the provision of achieving the precise adjustment required in calibrating the smoke detectors by an arrangement including means within the apparatus for engaging each of the potentiometer contacts, preferably by a screwdriver driven by an individual motor for each of the detectors. Further included is a control arrangement on the synchronous motors so that they are turned counterclockwise to reach a zero position on the command of suitable electric components and are then, at the appropriate calibration time, turned clockwise until a point is reached when the detector correctly gives its alarm indication. Whether or not each detector has given its alarm is monitored by a probe or similar device and a display indication is given to the operator of such successful calibration.

It is a further specific feature of the invention that independent flow channels are established for each of the groups of detectors under test. That is to say, when the smoke is being brought in for the purpose of calibrating and testing these detectors, the arrangement is such that the smoke is swept in by the operation of fans and uniform flow is promoted by a baffle assembly, the baffle assembly being so constructed that the flow of smoke is divided into independent channels and this channeling is preserved when the smoke is brought past the detectors which are arranged on a tiered or multilevel basis. Preceding the tiered basis or arrangement is a honeycomb device which further insures uniformity of the smoke mixture in each of the channels.

Yet another feature of the present invention resides in a technique, subsequent to carrying out the calibration of the smoke detectors, of exhausting the smoke used in the calibration stage, that is to say, of completely venting the enclosure; and thereafter instituting a test cycle which can be carried out in a much shorter time period inasmuch as one does not have to perform the operation of making the potentiometer adjustment, as in the calibration stage or cycle. Rather, one simply wants to check to determine if the calibration was done properly such that the devices again respond when the smoke obscuration reaches the predetermined level.

Other and further objects, advantages and features of the present invention will be understood by reference to the following specification in conjunction with the annexed drawing, wherein like parts have been given like numbers.

DESCRIPTION OF PREFERRED EMBODIMENT

Figure 1:
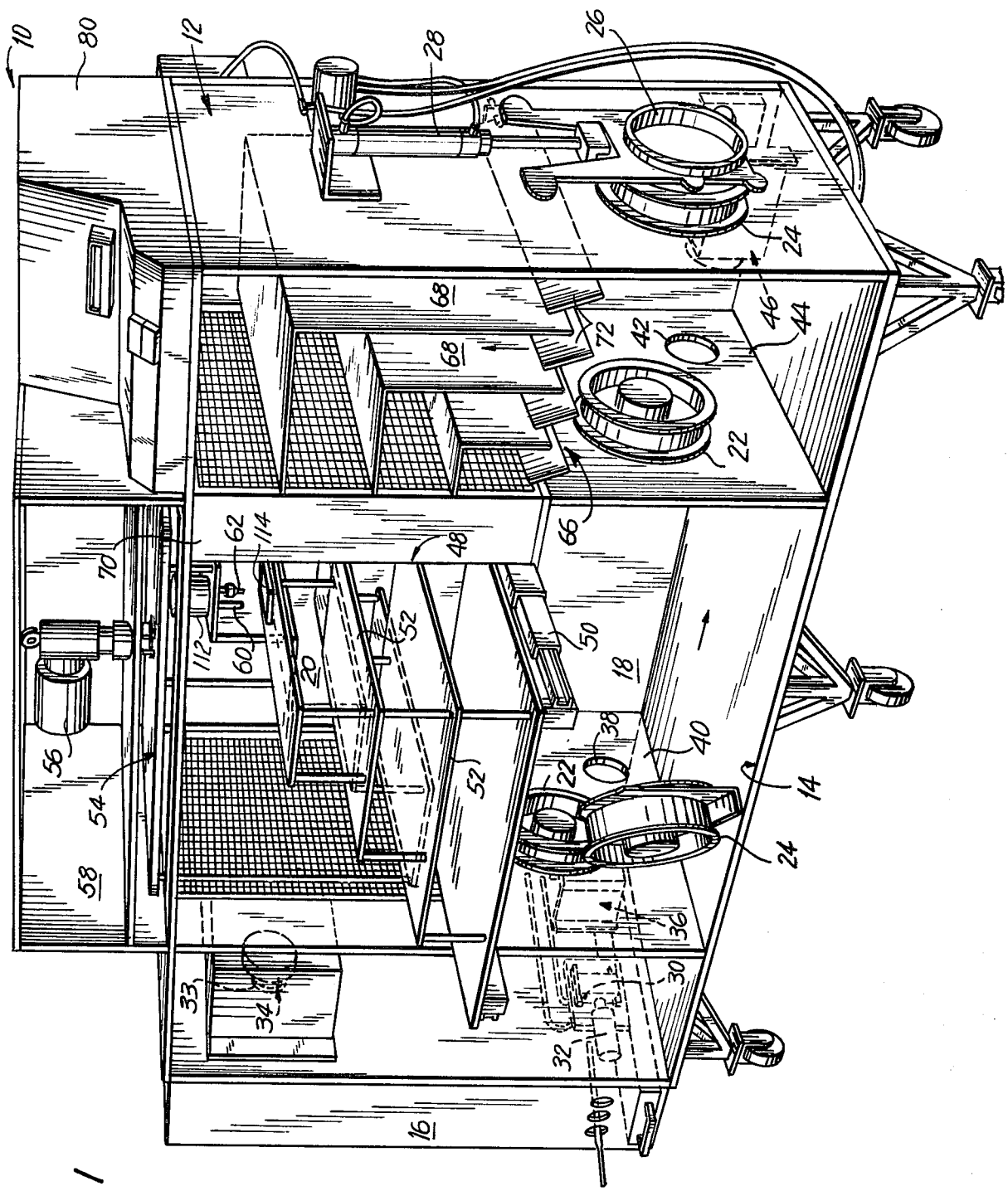
FIG. 1 is a perspective view of the preferred embodiment of apparatus for automatically calibrating and testing smoke detectors and the like, the front wall or cover having been removed to show the components within the enclosure.

Referring now to the figures of the drawing and for the moment to FIG. 1, there will be seen an apparatus 10 in accordance with a preferred embodiment of the present invention. This apparatus comprises an enclosure 12 defining a smoke chamber 14, such chamber being considered to take up the entire enclosure but being subdivided into several compartments.

The entire front side of enclosure 12 has been removed for ready understanding of the internal arrangement of parts and such front side includes a cover or door not seen. The smoke chamber 14 as noted is divided into a reserve smoke compartment 16 seen on the left in FIG. 1, a smoke mixing compartment 18 to the right of compartment 16, and a test compartment 20 immediately above the compartment 18. Located within and intercommunicating between compartments are a number of fans, two of which are mixing fans designated 22, the remaining two being exhaust fans 24 for purposes to be explained.

In connection with the transmission or movement of smoke throughout the test apparatus, there are provided a number of inlet or outlet ports. Thus, an exhaust port 26, and associated therewith a slide mechanism 28, are provided, as seen at the lower right in FIG. 1. A fresh air inlet port 30 and an associated slide mechanism 32 are seen at the lower left in the same figure. A smoke inlet port 33 and associated valve 34 are seen at the upper left.

In order that the operator may determine the degree of smoke obscuration, that is, obscuration of light by smoke, within the test compartment 20, a light source 36 is situated within the smoke mixing compartment, the light output therefrom being projected through an aperture 38 in a partition 40 dividing the two compartments. The beam of light so projected is sent through another aperture 42 in a partition 44 and is received by a photocell 46. This photocell is in the specific form of a photovoltaic cell, which generates a voltage, and by a suitable circuit arrangement, not seen, provides a current output for specific purposes to be described.

It will be noted that a drawer 48 is provided for retaining a plurality of groups of smoke detectors to be tested. This drawer is mounted for sliding movement into and out of the testing chamber, the slide being designated 50. As noted previously, a door is provided in the front panel for permitting sliding movement of such drawer 48 beyong the enclosure limits. The drawer is constructed to have a number of steps or tiers so that preferably a group of five smoke detectors can be disposed at each of four tiers 52.

Certain specific procedures are required in connection with the testing and calibrating of smoke detectors of the type described in copending application Ser. No. 647,018. Thus, a probe and motor block 54 is provided for two purposes: (1) to lower into position a plurality of individual motors, each being adapted to adjust the individual potentiometer of a particular smoke detector, and (2) to lower a probe for each of the smoke detectors so as to determine whether or not a given smoke detector has sounded its alarm or given its alarm indication. A control drive 56 for controlling the movement of probe and motor block 54 is seen located in a compartment 58 above the testing compartment 20.

It will be understood that a group of five motors is arranged at each level or tier of the motor block or rack so that a motor is normally poised at a place adjacent to a respective potentiometer contact for eventual engagement therewith. For the sake of clarity only representative motors have been shown in FIG. 1; likewise, only representative probes 60 have been illustrated. Attached to each of the individual motor shafts is a screwdriver 62 which makes the required engagement with the slot in the potentiometer control provided on the smoke detector.

In order to supply a density of smoke sufficient for calibrating and testing purposes and in order to promote uniformity of smoke density, the apparatus 10 is so arranged internally that the reserve smoke compartment 16 has an extremely dense supply of smoke therein. This is accomplished by having a good number of smoke punks or wicks burning so as to give off smoke within the compartment 16. Control over the actual density within the testing compartment is insured by the control furnished by smoke inlet valve 34. Accordingly, smoke at a predetermined required density can be realized from the dense smoke supply by reason of this control valve. Moreover, uniformity of smoke density is promoted by the internal arrangement involving mixing fans 22 and by reason of a baffle assembly 66 which breaks up the smoke flow into a number of channels 68 as will be appreciated from the configuration seen in FIG. 1. Thus these four channels or passageways are defined by the baffle assembly, and these channels are continued through an adjoining honeycomb airstream straightener 70 which further promotes uniformity of smoke density between the individual channels. It will also be seen that a series of louvers 72 is provided as part of the baffle assembly and these can be so adjusted as to regulate the flow in the individual channels 68. It will be understood that as seen in FIG. 1 the flow of smoke is in a counterclockwise direction as indicated by the arrows.

The apparatus in accordance with the invention for automatically controlling the calibration and testing of smoke detector devices further includes electrical equipment much of which is contained in a control box or console 80. For a full appreciation of the functioning of such electrical equipment, reference may be made to FIG. 2 in which a block diagram depicts the general layout or scheme of the entire apparatus or system. The test chamber 20 is seen with its several ports, that is, exhaust port 26, smoke inlet port 33, and fresh air inlet port 30. Each of the ports as already described is opened or closed by a valve including an air cylinder.

Figure 2:
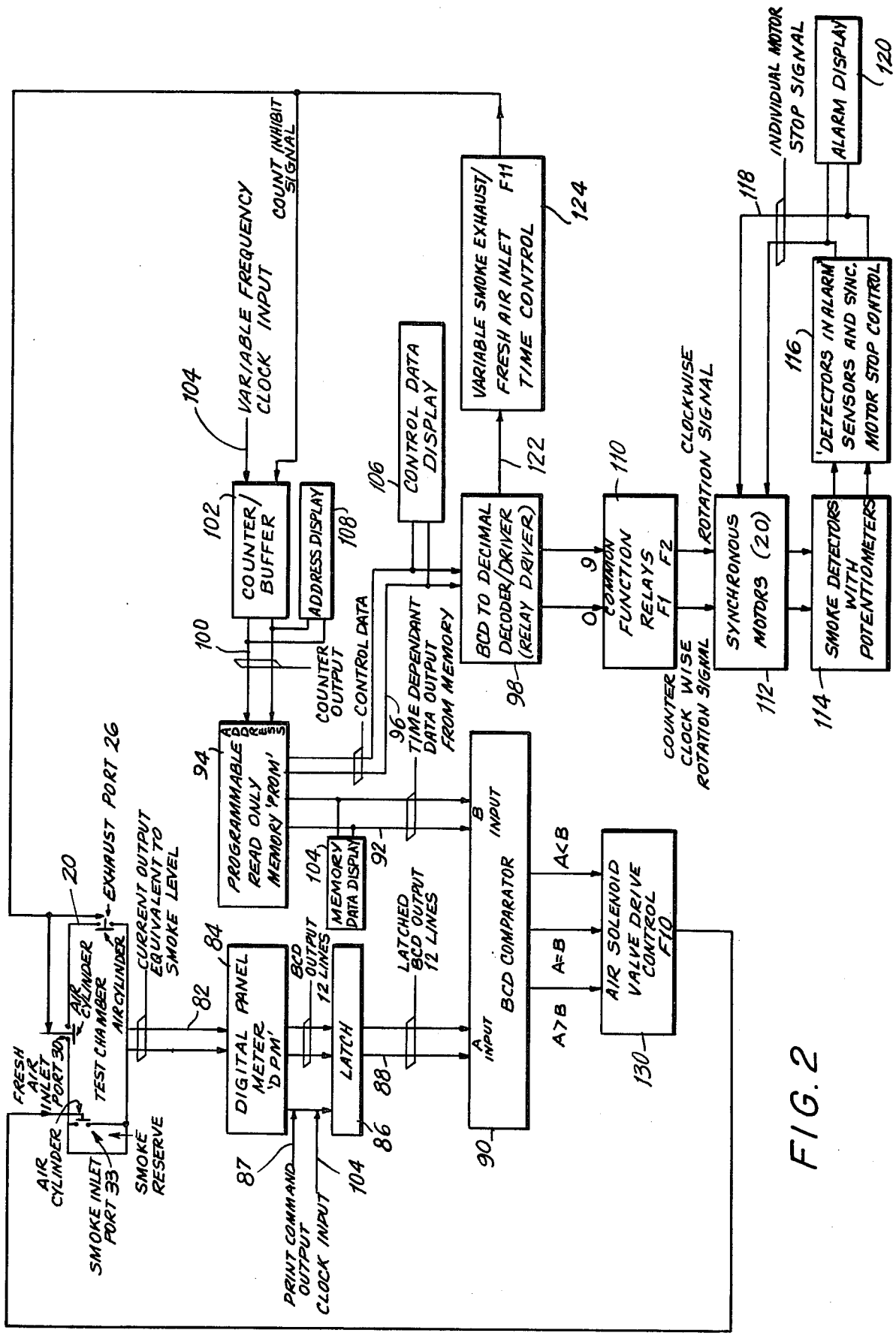
FIG. 2 is a block diagram of the components within said enclosure, and particularly showing the electrical components for automatically providing the required increase of visible smoke obscuration at a predetermined uniform rate.

Referring now to FIG. 2, a signal output from the already described photovoltaic cell 46 is applied by way of lines 82 to a digital panel meter or DPM 84. A binary coded decimal (BCD) output from the meter 84 is connected to the input of a latch 86, the latter being sometimes included as part of the digital meter. The output of latch 86 is continuously updated by reason of the print command output on an additional line 87 from DPM 84.

The output from latch 86 is connected by the lines 88, preferably twelve in number to handle the binary coded decimal output of twelve bits, to the A input of a comparator 90. This comparator performs the function of comparing two, 12 bit words; that is to say, it compares the 12 bit word coming to the A input from the latch 86 with the 12 bit word coming to the B input of the comparator 90, such B input being connected by lines 92 to a programmable read only memory or PROM 94.

The programmable read only memory 94 is designed to provide 32, 16 bit words. 12 bits of each word are main data bits which are taken to the comparator input B. The remaining 4 bits are for control functions. Thus, there will be seen the lines 96 which enable the control data bits to be transmitted to a decoder/driver 98 for converting from binary coded decimal to decimal and also for driving relays for functions to be described.

Also connected to PROM 94, specifically to the address section of such device, by way of lines 100, is a counter/buffer 102 that serves the purpose of counting pulses from a variable frequency clock input so as to provide an update at a predetermined rate of the data bits that should be furnished to the B input of the comparator 90. Since a variable frequency clock input is supplied on line 104, the addressing of PROM 94 and therefore the rate of change of smoke density can be altered by simply changing this input clock frequency.

It should be noted that each of the basic elements or components just described, that is, PROM 94, decoder/driver 98, and counter/buffer 102, has associated with it a display means such that the operator can be apprised of the state of each of these elements. Thus, PROM 94 has a memory data display 104; decoder/driver 98 has control data display 106; and counter/buffer 102 has address display 108.

The decoder/driver 98 operates to control a group of common function relays and the connections to a preferred number of ten relays is symbolized by the lines designated 0 and 9. In actual practice, only three or four of these common function relays are used and the others are retained as spares in the event they are required should the system be modified. The block containing the common function relays is designated 110. A significant one of these relays is F1 which when operable provides a signal to synchronous motors designated 112 such that these motors will be rotated in a counterclockwise direction. This is accomplished during the pre-calibration stage of the automatic calibration and testing technique. Another significant common function relay, indicated adjacent another output from block 110, is relay F2 which when operable provides for another signal to the individual synchronous motors 112. It should be noted that each of the twenty smoke detectors to be calibrated and tested is provided with its own synchronous motor and hence the numeral 20 within the block 112 corresponds to this number of motors. For the same reason, the two lines at the output from the block 112 to the block 114, which symbolizes the smoke detectors, are representative of twenty controls for adjustment of the potentiometers on the twenty detectors.

The synchronous motor for each of the potentiometer controls for the individual smoke detectors is controlled in its operation by conventional means or mechanisms. Thus, during the calibration stage when each of the smoke detectors being calibrated has its potentiometer control turned in the counterclockwise direction, this control is brought to the zero position at which point each shaft of the individual motors can slip until the operation is terminated. In the clockwise direction, each of the individual motors is controlled by a feedback arrangement which is illustrated in block form in FIG. 2. It will be seen that each of the aforementioned probe connections will operate as a sensor to detect whether a particular smoke detector is in the alarm state as symbolized by the block designated 116. By means well understood by those skilled in the art, an individual sensor determines whether an alarm current is flowing in a particular smoke detector device, and an individual relay operates suitable contacts responsive to that sensor to stop the respective calibrating motor. The motor stop signals are sent by way of the lines 118 extending from block 116 to block 112. At the same time that the motor stop feedback signals are being sent to block 112, an alarm display 120 indicates, by means of light emitting diodes or the like, that such has occurred.

In a preferred form of this alarm display 120, a pair of lamps, sometimes referred to as A and B lamps for each smoke detector, are provided. Thus the practice in accordance with the technique of the present invention is to turn on such a pair of lamps when the detector goes into its alarm state during calibration. Then, during the exhaust period all of the detectors that have gone into the alarm state should reset and at this time the A lamps must turn off while all the B lamps must stay on. Subsequently, all of the A lamps must turn on again for those detectors going into the alarm state during the test period.

Referring back to the decoder/driver 98, a connection by way of line 122 extends to a box designated 124 which symbolizes a control arrangement for providing a time variable smoke exhaust phase. Such phase involves (FIG. 1) opening the exhaust port 24 by means of the slide mechanism 26; operating the exhaust fans 24 and simultaneously therewith bringing in fresh air by operating the fresh air inlet port 30. This entire operation is controlled as indicated at the output of block 124 by relay F11, which is provided with appropriate contacts for the aforesaid purposes. In addition, a count inhibit signal is provided to counter/buffer 102 whenever relay F11 becomes energized. The control over this relay F11 can be completely understood by reference to FIG. 4 in which the details of the smoke exhaust time control can be appreciated. Therein will be seen the connection by way of line 122 from decoder/driver 98 to the time control 124. Included within the time control mechanism is a variable timer 125 which is implemented by integrated circuit chip 128 seen connected to a transistor 130 in the collector circuit of which the relay F11 is connected to the 24 volt power supply.

Figure 4:
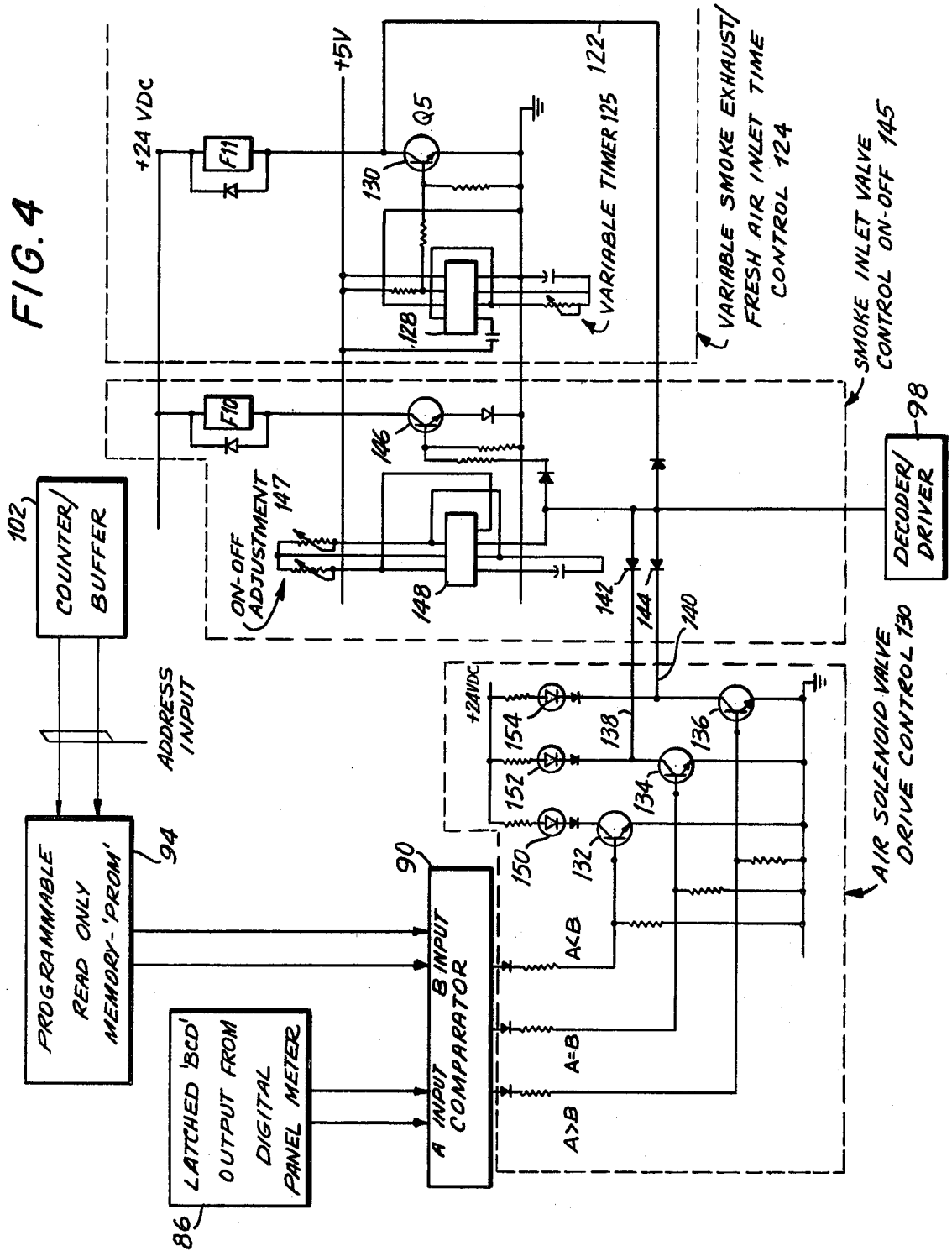
FIG. 4 is a block-schematic diagram which depicts in detail certain of the electrical components within certain of the blocks and shows the interconnections between such components and the other blocks depicted in FIG. 2.

Referring now to the BCD comparator 90, as seen in FIG. 2 and also in FIG. 4, three output lines are connected therefrom to an air solenoid valve drive control 130. The line on the left provides an output when the A input is greater than the B input. In this regard, it is to be especially noted that here the A and B inputs are referenced to percentage obscuration by smoke, rather than to microampere reading (the latter being inversely related to smoke obscuration). Similarly, the other lines provide outputs respectively when A equals B or A is less than B. The individual effects of each of the aforesaid results, that is of A being greater than B, equaling B or being less than B, can be appreciated by the detailed schematic diagram of FIG. 4 in which the circuitry within the box 130 is depicted. Thus it will be seen that the individual outputs from comparator 90 are taken to respective transistors 132, 134 and 136.

As will also be seen in FIG. 4, the output from the valve drive control 130 is connected by way of the lines 138 and 140 to the input of the smoke inlet valve ON/OFF control 145. This ON/OFF control mechanism includes an ON/OFF adjustment 147 and, by means of adjusting the resistance therein, the smoke inlet valve 34 can have an ON and OFF period suitable for providing the requisite density of smoke within the test compartment 20 and hence the required percentage of obscuration. What this means is that the adjustment can be effectuated such that the smoke inlet valve 34 is turned ON and OFF at a frequency sufficient to provide the smoke density required within the time period prescribed. Such control on relay F10, which is connected at the output of transistor 146, is established through an integrated circuit chip 148 which produces the selected ON/OFF timing for said relay.

It will thus be understood that the smoke inlet valve 34 is normally being constantly pulsed ON and OFF unless an appropriate output signal is received from the drive control 130. In the event that A is less than B and therefore that the smoke density is not high enough in the test compartment, the smoke inlet valve 34 will continue to be pulsed at the prescribed rate because, although transistor 132 is turned on at this time, no signal is transmitted to transistor 146. However, should the comparator 90 sense that A has become equal to B or A has become greater than B, then an appropriate output signal is transitted to the transistors 134 or 136. Consequently, either transistor 134 or transistor 136 becomes conductive and provides an output signal on the respective line 138 or 140, and thence by way of either diode 142 or 144 to the input of transistor 146 so as to prevent the turning on of transistor 146 and thereby to prevent energization of relay F10. In any event, that is, whether transistor 132, 134 or 136 has turned on, the corresponding light emitting diode 150, 152 or 154 will so indicate.

OPERATION

Figure 3:
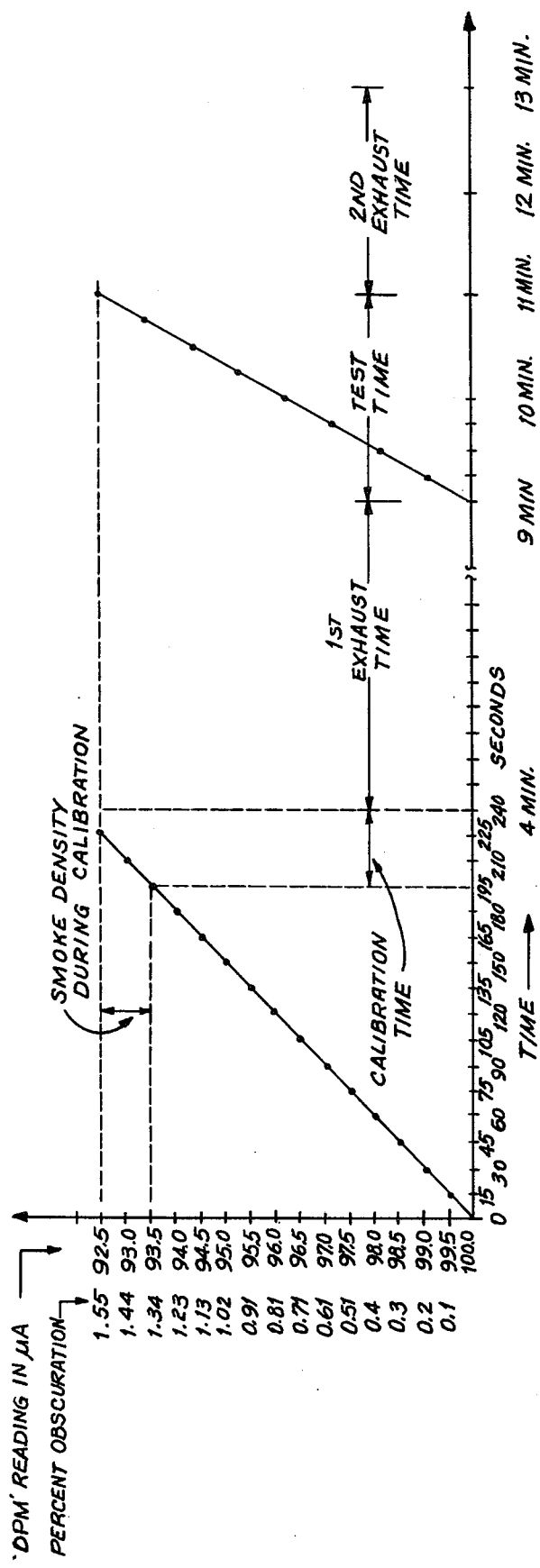
FIG. 3 is a graph depicting the percentage of obscuration, and also the corresponding digital panel meter reading in microamperes, at each moment of time during the calibration cycle, the first exhaust cycle, the test cycle, and the second exhaust cycle.

Assume that the detector test compartment 20 of apparatus 10 is filled with fresh air so that the digital panel meter 84 reads 100 microamperes at zero time (FIG. 3). The detectors to be calibrated are placed on the individual tiers 52. The drawer 48 is closed and the motor block 54 is lowered into position so that each of the probes 60 and screwdrivers 62 is located above the respective potentiometer in each detector.

When the cycle is started, the first address (0) appears at the input of PROM block 94 which is programmed so that its output is first given as 99.5 microamperes. Such output is the next required current reading equivalent to the new smoke density required inside the test compartment. The comparator 90 compares the existing data; that is to say, it compares: (1) the current reading equivalent to the present smoke density in the test compartment, which is taken from the output of the DPM block 84 and the latch block 86, such output appearing at the input A of the comparator 90, with (2) the new data from PROM block 94 appearing at input B. Since the data at input A indicates that the smoke density present in the test compartment is less than that required, the "A < B" output of comparator 90 will go high. This means that the smoke density level inside the compartment should be increased, which further means that the ON/OFF control 145 on relay F10 should be left undisturbed since it is effective to produce the requisite smoke density increase at a uniform rate.

As a consequence of the result at the comparator output which indicates that A is less than B, the solenoid valve which operates the air cylinder indicated in block 20 acts to open periodically the smoke inlet port 33 between the reserve smoke compartment and the mixing compartment. As a result, the smoke enters into the test compartment until the data from DPM 84 appearing at the input A of comparator 90 equals the data at input B thereof. When this happens the "A = B" output goes high which thereupon causes closure of the smoke inlet port. The smoke density level remains at 99.5 microamperes for the first fifteen seconds. However, at the end of the first 15 seconds, the address input to PROM 94 changes to "1". This results in putting out a new set of data from PROM 94 on lines 92; consequently a similar action to that already described repeats and the process continues until the meter reading is 92.5 (FIG. 3).

During the first minute that the data from PROM 94 is being compared with data from DPM 84, the aforenoted 4 bits of control data on line 96 are being transmitted by way of decoder/driver 98 and the common function relay F1 so as to drive the twenty synchronous motors in a counterclockwise direction. During this time each spring loaded screwdriver coupled to its motor shaft will position itself into the corresponding potentiometer slot and turn that particular potentiometer until it reaches its zero position at which time the motor shaft will be allowed to slip.

When the meter reading of DPM 84 reaches 93.5 microamperes, the control data is then sent from decoder/driver 98 to common function relay F2, which has the function of enabling the driving of the twenty synchronous motors in the clockwise direction. This is accomplished by well-known connections to reversible synchronous motors. Thus, in the one case previously described involving driving in the counterclockwise direction, the connections are, by way of an individual relay contact, to one coil of each of the synchronous motors; whereas in the case now under consideration of clockwise rotation, the connections are, by way of another individual relay contact, to the other coil of each of the synchronous motors. The clockwise rotation is accomplished during the calibration cycle. The synchronous motors can continue to turn in the clockwise direction for a maximum time period of 45 seconds and during this time period they will make approximately one complete turn.

As will be seen in the graph of FIG. 3, during this calibration time period the smoke density level inside the test compartment will change from 93.5 to 92.5 microamperes. Any detector that goes into its alarm state before the 45 second time limit will, because of the feedback control already described, stop its calibrating motor from turning.

As previously noted any detector in the alarm condition turns on two lamps, one of which locks in and stays on, while the second lamp stays on only so long as the detector is in alarm. Once the detector comes out of the alarm state, this latter lamp turns off.

When the reading of DPM 84 reaches 92.5 microamperes, the variable smoke exhaust/fresh air time control 124 acts to open the fresh air inlet port 30 and exhaust port 26; at the same time exhaust fans 24 are turned on and it is insured, by appropriate relay contact arrangement, that the smoke inlet port 33 remains closed. The exhaust time period is set by means of the variable timer 125 and, as seen in FIG. 3, is of the order of five minutes for the first exhaust phase, the second exhaust phase being shorter by reason of the operator interrupting the exhaust operation. It is of course during the first exhaust phase or time that the detectors reset, thereby turning off one of the two lamps that were turned on during the alarm state achieved during the calibration time.

At the end of the first exhaust time period, an audible alarm calls the operator to make sure that all detectors have reset. A bad detector will not reset. The meter 84 returns to its original state and the fresh air inlet port and exhaust port are closed.

In order to test the detectors for valid calibration, and thus insure that the detectors will be reliable in service, the smoke level is again increased in the same manner as already described. However, the desired reading of 92.5 microamperes is reached in a test time period of approximately only 2 minutes. This is accomplished by increasing the frequency of the clock input. When the detectors have again reached the state in which they should give an alarm, the second alarm lamp for each detector will turn on again. The operator can now visually verify the new alarm indication with the previous one and can note down bad detectors so that they can be distinguished from the good ones.

At the end of this test time period, the exhaust operation is again instituted for a second exhaust time period so as to remove all of the smoke from the chamber. The operator can then remove the calibrated detectors and the chamber is ready for the second set or batch to be tested.

What has been disclosed is a simple and efficient apparatus for thoroughly calibrating and testing smoke detector devices. This apparatus and the attendant techniques developed are able to provide a very accurate rate of increase in smoke levels within the test chamber — a very desirable goal, as explained, in the calibration and testing of smoke detectors. The rate of change of smoke density can very easily be altered by simply changing the input clock frequency of the system. Moreover, desired incremental change in the smoke level can be effected by changing the program of a programmable read only memory.

In addition to the above advantages, visual displays of the current smoke levels from a meter, which affords a reading of the smoke level within the smoke chamber, vis-a-vis the smoke level from the read only memory, are readily available for verification. The system also affords the operator the facility for calibrating precisely all of the detectors in a very short time period of the order of 45 seconds, and of carrying out the entire required calibrating and testing operation in less than 15 minutes.

While there has been shown and described what is considered at present to be the preferred embodiment of the present invention, it will be appreciated by those skilled in the art that modifications of such embodiment may be made. It is therefore desired that the invention not be limited to this embodiment, and it is intended to cover in the appended claims all such modifications as fall within the true spirit and scope of the invention.

What is claimed is:

1. Apparatus for the testing of smoke detector devices, comprising
   an enclosure defining a smoke chamber;
   means for measuring the light obscuration produced by varying levels of smoke in said chamber, said means for measuring including a light source and a photocell for sensing the light output from said source;
   means for automatically increasing the obscuration in said chamber at a predetermined uniform rate, including means for comparing the obscuration due to a current or instantaneous level of smoke in the chamber with a programmed level, and
   means for regulating or gating the intake of smoke to said chamber so as to reach the programmed level within a predetermined time period.

2. Apparatus as defined in claim 1, further comprising means for calibrating groups of smoke detectors under test, said means for calibrating including means for adjusting each of the smoke detectors as the smoke obscuration level reaches a desired calibration range such that the smoke detectors under test will normally provide an alarm indication, and means for sensing whether each detector has in fact been properly calibrated.

3. Apparatus as defined in claim 1, in which said smoke chamber comprises a reserve smoke compartment, a mixing compartment, and a test compartment.

4. Apparatus as defined in claim 2, further comprising a smoke inlet valve, and a drive control means connected to said comparing means so as to control said valve.

5. Apparatus as defined in claim 3, in which a smoke inlet port is situated between said reserve smoke compartment and said mixing compartment.

6. Apparatus as defined in claim 1, further comprising a read only memory and common function relays, and in which a relay driver means is connected to the output of said read only memory such that control data bits transmitted from said read only memory to said relay driver means will control said common function relays.

7. Apparatus as defined in claim 6, in which at least a pair of relays is included as part of said common function relays, one of said pair of relays being operable to permit energization of a group of synchronous motors for controlling the adjustment means on each of said detectors, said one relay being operable to cause the counterclockwise rotation of all of said synchronous motors prior to reaching the calibration time period during said testing cycle.

8. Apparatus as defined in claim 7, further comprising a probe connection for each of said smoke detectors for sensing whether or not said smoke detectors are in the alarm state, including means for feeding back a signal representative of such alarm state so as to stop the clockwise rotation of a respective motor of a predetermined smoke detector when said detector is in the alarm state.

9. Apparatus as defined in claim 2, further comprising a slidable drawer having a plurality of tiers for holding said groups of smoke detectors.

10. Apparatus as defined in claim 9, further comprising a baffle assembly within said enclosure for establishing individual channels having uniform smoke density.

11. Apparatus as defined in claim 9, further comprising a rack for holding groups of synchronous motors, and means for moving said motors into position to engage respectively with said groups of smoke detectors.

12. Apparatus as defined in claim 2, further comprising a smoke inlet port, a fresh air inlet port and an exhaust port;
means for exhausting smoke from said smoke chamber, including means for opening said fresh air inlet port and said exhaust port, and insuring that said smoke inlet port remains closed.

13. Apparatus as defined in claim 2, in which said means for regulating the intake of smoke includes a smoke inlet valve and means for controlling the ON and OFF periods for said smoke inlet valve.

* * * * *